United States Patent [19]
Morelli et al.

[11] Patent Number: 5,112,555
[45] Date of Patent: May 12, 1992

[54] METHOD OF FORMING BANDED CONDOMS

[75] Inventors: Harold A. Morelli, Wyckoff; Eugene K. Lubbs, Milford, both of N.J.

[73] Assignee: Schmid Laboratories, Inc., Little Falls, N.J.

[21] Appl. No.: 516,921

[22] Filed: Apr. 30, 1990

Related U.S. Application Data

[63] Continuation of Ser. No. 154,893, Feb. 11, 1988, abandoned.

[51] Int. Cl.⁵ .............................................. B29C 41/14
[52] U.S. Cl. ........................ 264/271.1; 264/296; 264/302; 264/305; 264/310
[58] Field of Search ............ 264/305, 302, 303, 271.1, 264/294, 295, 296, 310; 425/275

[56] References Cited

U.S. PATENT DOCUMENTS

| | | | |
|---|---|---|---|
| 1,152,372 | 8/1915 | Miller | 264/305 |
| 2,017,604 | 10/1935 | Mountford et al. | 264/305 |
| 3,553,308 | 1/1971 | Kobayashi | 264/305 |
| 4,100,309 | 7/1978 | Micklus et al. | 427/2 |
| 4,406,853 | 9/1983 | Miyata | 264/304 |
| 4,432,357 | 2/1984 | Pomeranz | 604/346 |

Primary Examiner—Robert A. Dawson
Assistant Examiner—Allan R. Kuhns
Attorney, Agent, or Firm—Darby & Darby

[57] ABSTRACT

A method and apparatus for banding collagen condoms. An elastic band is incorporated into the collagen gel body of the condom as an integral part thereof. The band is sealed within adjacent layers of collagen film, made from collagen gel, the layers of film forming the condom body.

12 Claims, 4 Drawing Sheets

METHOD OF FORMING BANDED CONDOMS

This is a continuation, of application, now abandoned Ser. No. 154,893, filed Feb. 11, 1988.

This invention relates to collagen condoms with flexible elastic banding that provides improved characteristics during use. The invention also relates to a method and apparatus for banding collagen condoms.

BACKGROUND OF THE INVENTION

It is desirable that a condom be held firmly and comfortably in place during use. Natural rubber or synthetic elastomer condoms, because they are highly elastic, are made smaller than the erect penis. These condoms are designed to stretch slightly when put on, and to contract firmly around the penis while being worn. The condom is held in place in this way during intercourse. These condoms are satisfactory in strength and thinness, and can be economically manufactured. However, they are notably inferior in sensitivity, are water impermeable, and are ineffective heat conductors. The elastic material relied upon to keep the condom in place often results in discomfort, is unduly dependent on the size of the penis, is known to become brittle, tear or fail during use more often than other types of condoms, and may deteriorate in the presence of commonly used petroleum-based lubricants.

Condoms made from natural membranes, such as lamb cecum, are satisfactory in strength and thinness, and offer improved sensitivity, permeability, and comfort. These condoms are virtually inelastic, and therefore must be made somewhat larger than the erect penis. To hold the condom in place, a slit is cut on each side of the open end of the condom, forming two flaps which can be folded down over an elastic band and glued in place. This simple gluing process can be used because the membrane is dry, and because it is supple due to the plasticizing effect of naturally occurring fat. Thus, the condom is held in place by an elastic band having a circumference adapted to contract around the penis, and not by contraction of the condom body.

In one banding method, the dry tubular cecum is placed mitten-like over a wide flat form, which flattens the condom. Starting at the top open end of the condom, slits about one-half inch long are cut on each side of the flattened membrane, making two flaps. A rubber band is place over each cecum and is positioned just below, or at the apex, of the slits. Glue is applied in a stripe to both sides of the flattened condom. The flaps are folded over the rubber band and pressed into the glue. When the glue is dry, the condom is removed from the form and is wetted prior to subsequent processing.

This banding method requires that each condom be individually handled, and there is a high risk that incipient tears at the apex of the condom, at or near the slits, will occur during processing. In addition, natural ceca are limited in availability and cecum condoms are expensive to manufacture. The final product also suffers from unavoidable surface irregularities which remain after processing of the thin natural membranes.

Efforts to develop condoms having the desirable strength and comfort characteristics of ceca-based products, but at a lower cost and without dependence on a natural resource of increasing rarity, have led to the development of collagen-based condoms, made from collagen gels. Homogeneous collagen gels capable of forming smooth films of uniform strength, and suitable for use as a condom material, are disclosed in applicant's U.S. Pat. No. 4,626,286, the subject matter of which is incorporated herein by reference. Collagen condoms and methods for manufacturing them are also disclosed in U.S. Pat. No. 4,406,853 and No. 4,349,026.

Thin film articles made from collagen gels have superior breaking and tear strength, and improved homogeneity, thinness, smoothness, sensitivity and appearance. They are also convenient and economical to manufacture.

Collagen condoms are formed by repeatedly dipping a phallic mandrel into an aqueous collagen gel, withdrawing the mandrel and drying the resulting coating. The dipping process is repeated until a collagen film having the desired thickness is obtained. In one embodiment, the mandrel may be rotated in two directions, to achieve a film that is uniformly strong in both directions.

Collagen condoms must be moist in order to readily remove them from the dipping mandrel, and they remain moist throughout subsequent processing and sale.

Collagen condoms are inelastic, like those made from ceca, and they are made larger than the erect penis. A reliable means of holding the condom in place during use is therefore needed, but the known banding means have been unsatisfactory. Glue cannot be applied to the collagen condom while it is wet. When dry, the condom material tends to be brittle, because the regenerated collagen film contains no fat. Efforts to slit and fold the dry brittle film for the known gluing process often result in tears and fractures in the condom. To delicately remove each condom from its mandrel while dry, and glue each band in place individually according to the known method, followed by a rewetting step for processing, is difficult and costly. Collagen condoms also cannot be banded merely by rolling the top of the condom before curing, using the techniques heretofore employed for banding latex condoms.

These problems and disadvantages have been overcome, according to the present invention, by advantageously incorporating an elastic banding means into the condom during the dipping process.

OBJECTS OF THE INVENTION

It is an object of the invention to provide a strong, thin, resilient, and homogeneous regenerated collagen gel condom having a circumferential integral elastic band firmly and integrally incorporated therein, thereby achieving a product that is low in cost, but superior in strength, comfort and reliability.

It is another object of the invention to provide a novel and advantageous method of banding collagen condoms.

It is yet another object of the invention to provide an apparatus for banding condoms according to the method of the invention.

These and other objects of the present invention will be apparent to those skilled in the art, in light of the accompanying description, drawings, and appended claims.

SUMMARY OF THE INVENTION

Prior to dipping a phallic-shaped mandrel into a bath of collagen gel, an elastic band is placed at the top of the mandrel, away from the blunt tip. The mandrel is then dipped blunt-end first and coated with gel, to a depth just short of the elastic band. The gel is dried into a film, preferably in a drying tunnel. In a preferred embodiment, the mandrel is plastic or glass and may also be tapered toward the head to aid removal of the finished condom from the mandrel. In another embodiment, the dipping step may be achieved by raising a tank containing the collagen gel up and over the blunt tip of the mandrel, until the mandrel is submerged in the gel to the desired depth. This process is repeated as often as desired, to obtain a continuous film of desired uniform thickness and open at the top, thus forming a collagen condom. Preferably, 2-3 coats of collagen gel are applied. In a preferred embodiment, the mandrel is rotated during the application of each gel coat, and the direction of rotation can be reversed after each application.

When the desired number of gel coats have been applied and dried, the elastic band is rolled over the integrated layers of film and positioned near the top of the open end. Water is applied to at least a portion of the film above the band, using a spray, moistened sponge, brush, or similar applicator. This softens the film and makes it flexible. A coating of gel is applied with a brush or similar applicator below and optionally above the band. An upper flap comprising the moist flexible film is folded down over band and pressed against the gel coating below the band. One or more additional coats of gel, extending over the entire band position, are applied to the entire mandrel by dipping, withdrawing and drying as previously described. In this manner, the band is enfolded and sealed, and becomes an integral part of the condom. This method is suitable for either rolled or folded condoms.

In a preferred embodiment, particularly for folded condoms, the mandrel is advantageously provided with a cone-shaped portion at the top, which improves the band enfolding step. In another embodiment, specifically for rolled condoms, the cone extension to the mandrel is not necessary, the intermediary application of water and gel can be omitted, and the upper flap need not be folded over the band. Instead, additional coats of gel are applied to the mandrel directly over the band, and when processing is completed, the upper region of the moist condom incorporating the band is rolled down to create a donut-shaped item ready to be unrolled over the erect penis.

DETAILED DESCRIPTION

The present invention provides a method for producing condoms comprising collagen films having an integral elastic band. First, a collagen gel is prepared and an elastic band is placed at the upper end of a phallic mandrel having a lower blunt end. Second, a set of primary coats of collagen gel are sequentially applied to the mandrel (not to the elastic band) and each coat is dried into a homogeneous layer, to form a condom body. Third, the elastic band is lowered over the condom body to a predetermined position, water is applied to at least a portion of the film above the band, and a stripe of collagen gel is applied to the condom body below and optionally above the band. Fourth, the uppermost portion of the condom body is folded over the elastic band in the form of a continuous flap, so that the band is enfolded and enclosed by the flap, which bonds with the condom body along the stripe of gel. Finally, additional coats of gel are applied to the condom body, over and including the flap and the enfolded elastic band, to complete the condom body and integrally seal the flap and band within the finished condom.

EXAMPLE 1

Preparation of Collagen Gel

The condoms of the invention are made using a collagen gel. Collagen gel was prepared from Bovine digital flexor tendon, which was ground through a plate with 3/16" diameter holes. From coarsely ground tendon containing 35.69 kg solids, a 853.79 g portion was dispersed into 13.62 kg of water at 15 degrees C., to which had been added 0.128 g of the enzyme Rhozyme-41. The total dispersion was passed once through a Stephen Microcutter with a 1 mm blade clearance. The comminuted mass was allowed to stand at 24 degrees C. to allow the enzyme to work. After 17 hours, 11.99 kg $H_2O$ containing 183 g starch, 17.5 ml formaldehyde (5%) and 140 ml lactic acid (88%) was stirred into the enzyme treated slurry. The resulting acidified mass was passed once through the microcutter to enhance swelling and to homogenize the resultant gel. The homogenized gel was transferred to a Ross planetary mixer and stirred under vacuum for 20 minutes to remove entrained air. The gel had a solid content of 2.17% and a viscosity of 2760 cps.

EXAMPLE 2

Preparation and Banding of Folded Condoms

Figure 1A:
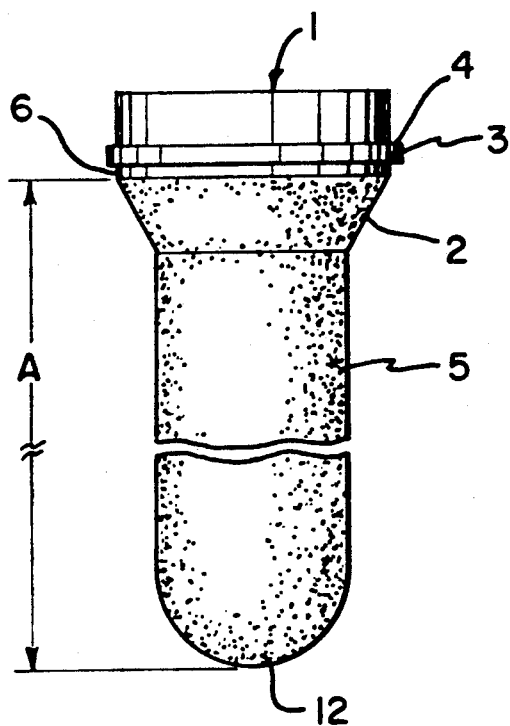
FIG. 1a-1d is a schematic view of a banding method for folded condoms, according to the invention.

With reference to FIG. 1a, a ceramic, glass or plastic mandrel 1 with a blunt or phallic tip 12 and an enlarged cone-shaped portion 2 at the upper end is used for making banded condoms. Before dipping, a rubber band 3 with a 3" circumference and a 0.063" square cross section is placed on the mandrel in a first band position 4, above the cone-shaped portion 2. Three primary coats of gel 5, prepared according to Example 1, are applied to the mandrel 1, up to a first dipping position 6 below the first band position 4, show in FIG. 1a as the region A.

In a preferred embodiment, the first dipping position 6 is the top of the cone-shaped portion 2. Each gel coat is applied by dipping the mandrel 1 into the gel, withdrawing it from the gel at a speed of 1.83 inches/second, while rotating the mandrel 1 about its vertical axis at about 0.115 revolutions/inch of vertical travel. The direction of mandrel rotation is changed for each dip. After each dip the gel coating is dried for about 15 minutes in a stream of air at 80 degrees C. (not shown).

The dipping and withdrawing steps can also be achieved by raising a tank containing the gel up and over the blunt end of the mandrel 1, until it is submerged to the depth of the first dipping position 6. Each dip lasts approximately 30 seconds. In the embodiment using the raised tank, the tank should move upward at a slow speed upon fist contact of the gel with the mandrel, whereafter the dipping speed can be increased. The mandrels can be rotated during dipping into and withdrawal from the gel.

Figure 1B:
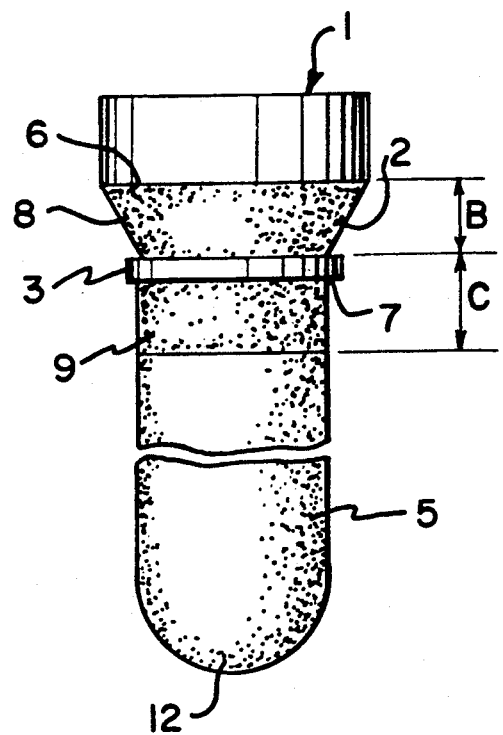

After the third coat of gel is applied and dried, the band 3 is rolled down over the three layers or primary coats 5 of dried film to a final band position 7 as shown in FIG. 1b, at the bottom of the cone-shaped portion 2 of the mandrel 1. Using a moistened sponge, water was applied to a flap portion 8 of the film defined by the band 3 and the first dipping position 6, shown in FIG. 1b as the region B.

In a preferred embodiment, the flap portion 8 covers the cone-shaped portion 2. Water is applied to soften the dried gel or film forming the flap portion 8 and make it flexible. Then, with a brush, a ½ inch wide strip 9 around the mandrel 1 and immediately below the band 3, shown in FIG. 1b as the region C., is coated with the same collagen gel employed in the dipping step.

Figure 1C:
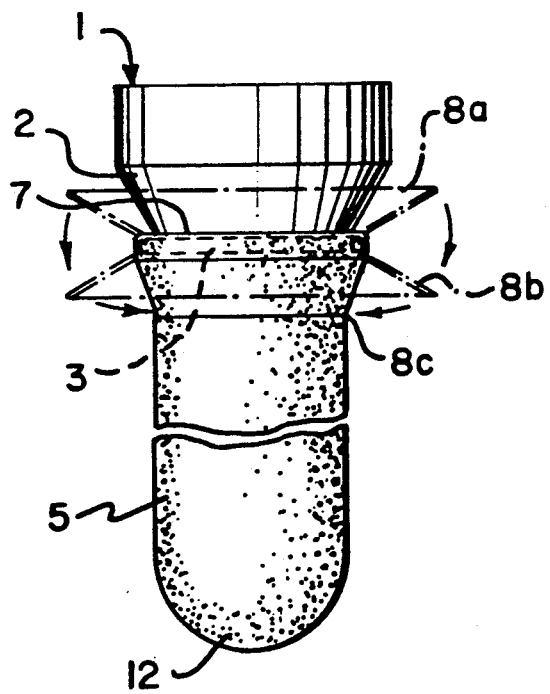

Referring to FIG. 1c, the moistened, supple flap portion 8, overlying the cone, is folded down over the band 3 from a first flap position 8a through a plurality of intermediate positions illustrated as 8b, to a final flap position 8c. In its final position 8c, the flap portion 8 is pressed against the gel strip 9 below the band 3 to enclose the band within the flap portion 8.

Figure 1D:
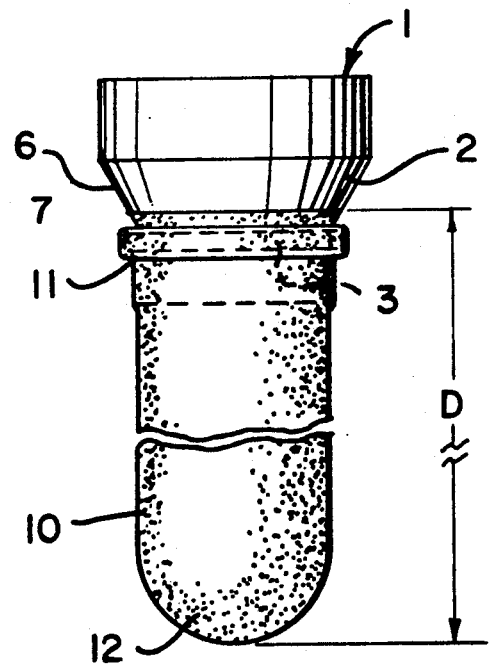

Two more secondary gel coats 10, extending about ¼ inch above the band 3, shown in FIG. 1d as the region D, are applied and dried in the manner already described, sealing and incorporating the band 3 within an envelope region 11. The final product, when removed from the mandrel 1, comprises a banded condom according to the invention.

After dipping, and especially after the final dip, the gel may be treated with about 0.25% ammonia and rinsed with deionized water. The gel may also be treated with glutaraldehyde, as a tanning agent.

EXAMPLE 3

Preparation and Banding of Rolled Condoms

Figure 2A:
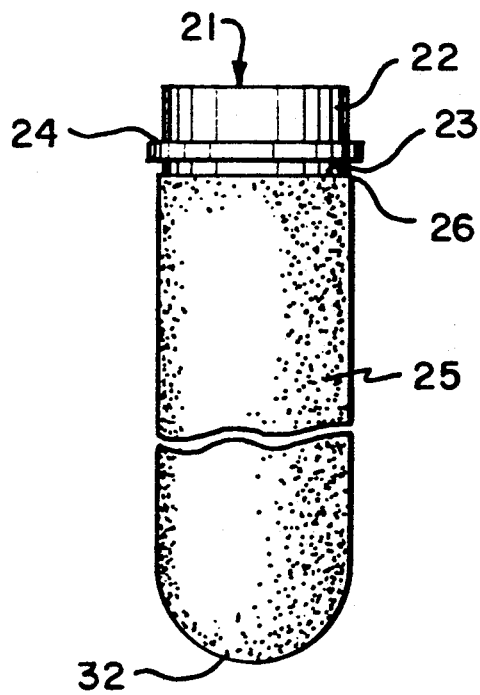
FIG. 2a-2c is a schematic view of a banding method for rolled condoms, according to the invention.
Figure 2B:
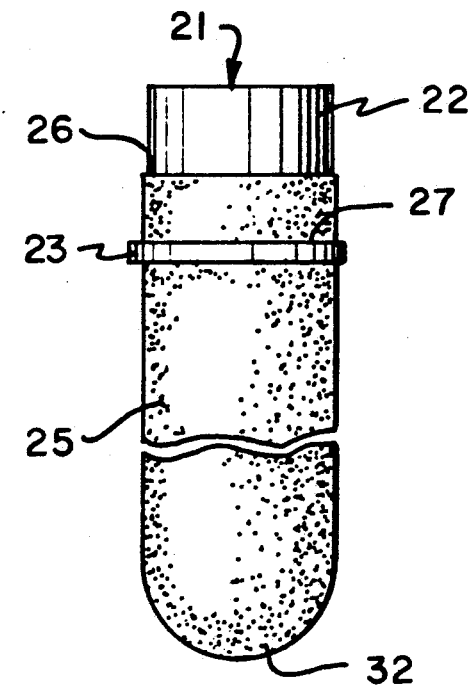
Figure 2C:
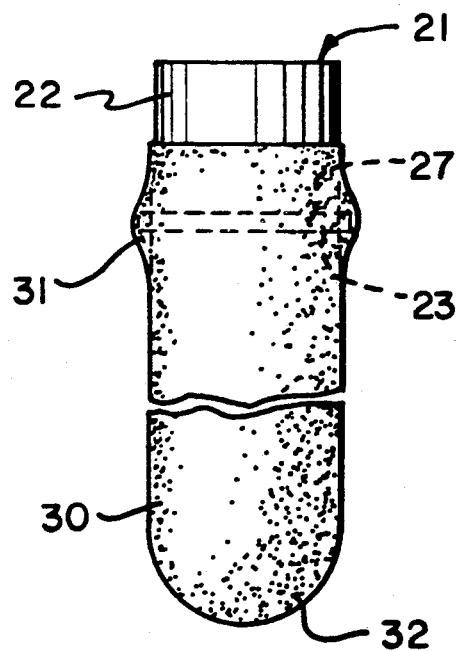

A collagen gel is prepared according to Example 1. Referring to FIG. 2, a ceramic, glass or plastic mandrel 21, without the cone-shaped portion, but having a top portion 22 and a tip 32, was used for an alternate banding method. As shown in FIG. 2a an elastic band 23 of the type previously described is placed on the phallic mandrel 21, approximately 10 inches up from the tip, in a first band position 24. Two primary layers of gel 25 are formed on the mandrel 21 by dipping, withdrawing and drying according to the method previously described. The mandrel 21 is dipped into the gel to a depth of 7½ inches, to a first dipping position 26. After the second primary gel coat 25 is dry, the band 23 is rolled down over the dry film to a final band position 27, 7 inches above the mandrel tip 32, as shown in FIG. 2b. Three secondary gel coats 30 were applied to a level ¼ inch above the band 23 and dried in the manner described, and as illustrated in FIG. 2c. Thus, the band 23 was incorporated into the structure of the final condom product, within an envelope region 31.

After the final gel coat was dried, the mandrel was treated with a 0.25% ammonium hydroxide solution for 3 minutes, and then was washed with deionized water for 6 minutes, followed by treatment with a 0.06% glutaraldehyde solution for 3 minutes and a final 3 minute rinse with deionized water. After the final rinse, the banded condoms were removed from the dipping mandrels and washed for 30 minutes in deionized water.

EXAMPLE 4

Apparatus for Banding Collagen Condoms

Figure 3A:
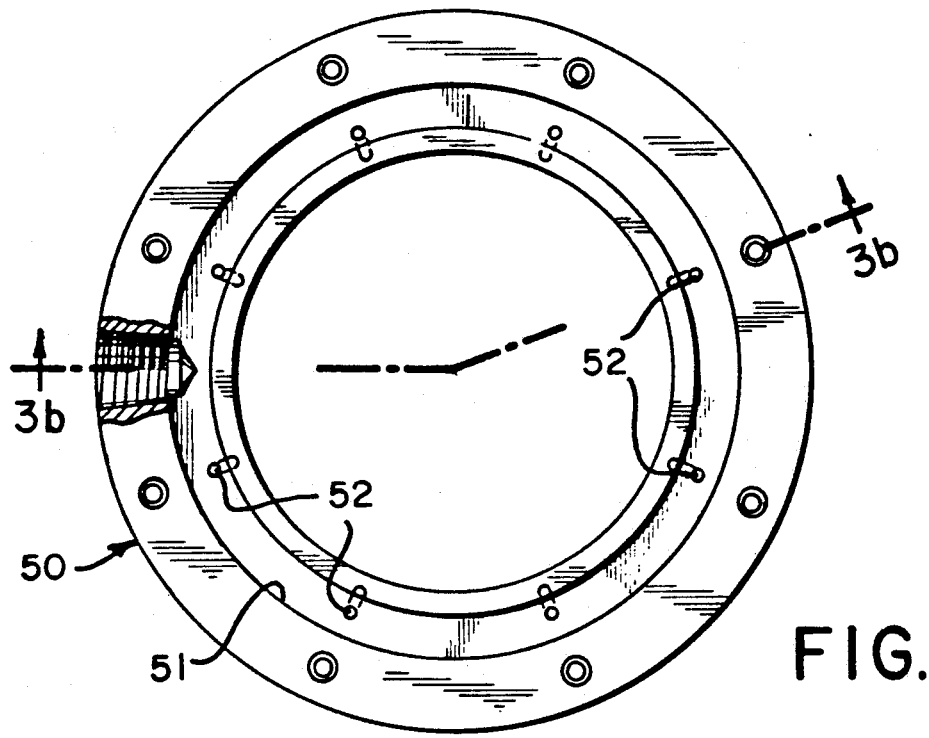
FIG. 3a is a plan view of an apparatus for banding condoms according to the invention.
Figure 3B:
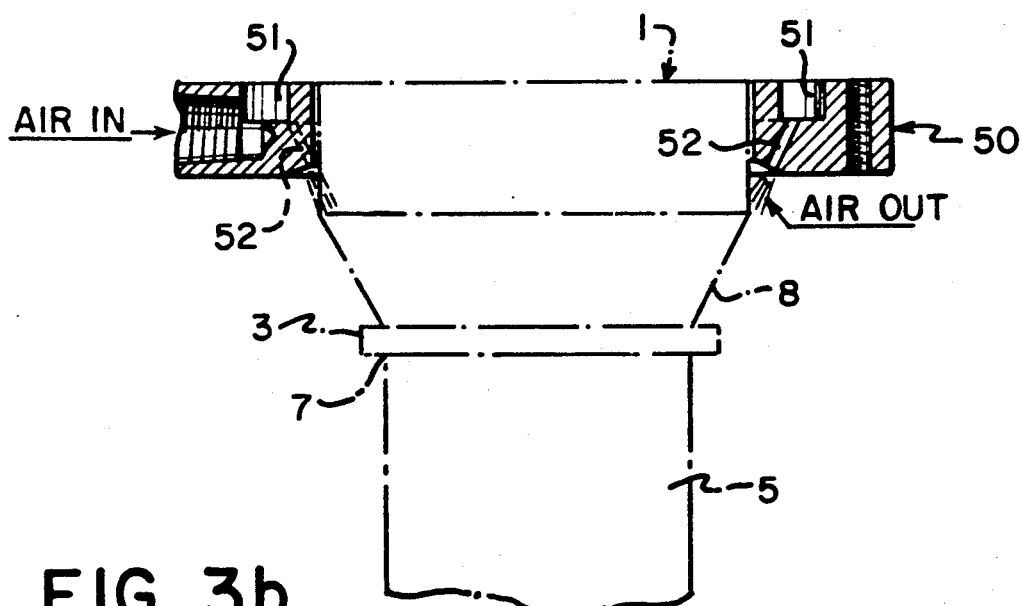
FIG. 3b is a side view of an apparatus for banding condoms according to the invention.

In a preferred embodiment, the flap portion 8 is folded over the band 3 with the apparatus of FIG. 3a and 3b. A compressed air ring 50 is raised over the dried primary coating 5, past the band 3 in its final position 7, with the air off. The air ring has an annular groove 51 with feeding holes 52 which selectively blow against the mandrel 1 at an angle chosen to direct the air at and then under the upper leading edge of the condom body and flap portion 8, preferably of 30 degrees. When the compressed air is turned on and the ring 50 is lowered, it confronts the upper portion of the mandrel and the upper leading edge of the flap portion 8, and acts to separate the flap from the mandrel, and to push the flap down and over the elastic band 3. The flap 8, which has been turned inside out, then seizes against the condom body and the primary coats 5, within the region C of FIG. 1b. The air is pressurized, preferably at 70–80 PSI.

When the flap portion 8 seizes against the condom body, the air ring 50 continues its descent and exits the mandrel 1 at its tip 12. The mandrel 1 is then dipped again, as described, until in a preferred embodiment the resulting condom product has five gel layers with an integral flap portion 8 enveloping the band 3 within an envelope region 11, thereby affording maximum resistance to band separation by unusual tugging force.

EXAMPLE 5

Automated Banding Apparatus

Figure 4:
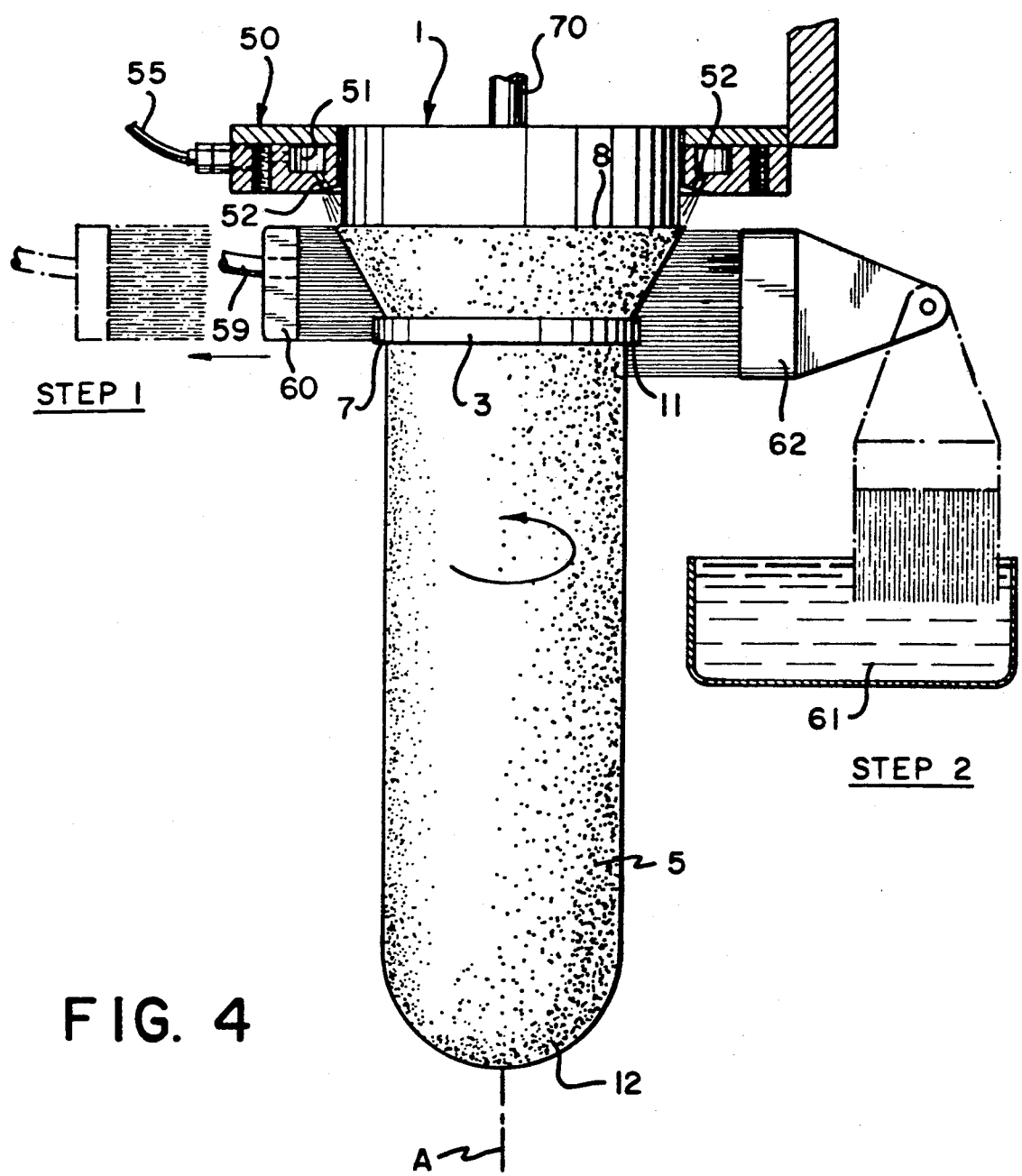
FIG. 4 is a schematic view of an automated apparatus according to the invention.

The air ring 50 can be raised and lowered manually, or by motorized or pneumatic means, and indeed the entire apparatus can be automated by conventional means. One such means is schematically illustrated in FIG. 4.

The air ring 50 is mounted on a supporting armature (not shown) which serves to raise and lower the air ring 50 about a central axis A, which corresponds with the central vertical axis 70 of the mandrel 1. After the primary gel coat 5 are applied to the mandrel 1 in the manner previously described, and the band 3 is lowered to its final position 7 the air ring 50 is raised up and over the bottom of the mandrel along the axis A, by conventional pneumatic means, from a rest position (not shown) below the mandrel to a ready position above the flap portion 8 (shown).

When the ring 50 is in the ready position, a water supply means 59 supplies water to a water applicator 60, which selectively moistens the primary coats 5 within a region proximate to the band 3 and generally coextensive with the flap portion 8. In the embodiment shown, the water applicator 60 moves by conventional means into an operative position proximate to the flap region 8 after the air ring 50 reaches its ready position.

After the primary coats 5 of the flap region 8 are moistened, a gel applicator 62 moves by conventional means into an operative position proximate to the flap region 8. The gel applicator 62 is supplied with collagen gel by a gel supply 61. In the embodiment shown, the gel applicator 62 is a brush, which applies one or more stripes of gel to the primary coats 5 within a region proximate to the band 3 and generally coextensive with the flap portion 8.

In a preferred embodiment, the mandrel 1 is rotated about the axis A by the shaft 70 during the application of water by the water applicator 60 and the application of gel by the gel applicator 62. The water applicator 60 and gel applicator 62 are supported by conventional structural elements which are not shown in the figures.

When the band 3 and flap portion 8 are moistened with water and striped with gel, the air ring 50 is activated while in its ready position. First, compressed air, preferably at 70-80 PSI is supplied to an annular groove 51 (FIGS. 3a and 3b) by an air supply means 55. The compressed air is circumferentially directed through feeding holes 52, which direct a plurality of air streams at the upper surface of the mandrel 1, and at the leading edge of the flap portion 8 of the primary coats 5. The position of the ring 50 and the angle of the holes 52 are chosen so that the air streams are directed between the leading edge of the flap portion 8 and the mandrel 1, causing the flap portion 8 to separate from the mandrel 1. Contemporaneous with this separation, the air ring 50 is lowered over the mandrel 1 and the primary coats 5, with the air on, so that the flap portion 8 is pushed downward and is folded over the elastic band 3, to form a continuous envelope of gel around the band 3. When the flap portion 8 is folded, it is turned inside out, so that its outer surface becomes an inner surface that is pressed into contact with the pre-moistened and gel-striped region of the primary coats 5 proximate to the band 3. In this manner, the flap portion 8 is sealed around the band 3 in the form of a continuous envelope.

The compressed air may be turned off once the air ring 50 is lowered past the folded flap portion 8, and in a preferred embodiment the mandrel 1 is not rotated during the folding step, i.e. while the compressed air is on.

Once the air ring 50 is turned off and lowered past the mandrel 1 and back to its ready position, additional coats of gel are applied and dried over the mandrel, including the flap portion 8 and the band 6, in the manner described in previous examples, but not shown in FIG. 4. In this manner, the elastic band 3 and flap portion 8 are integrally sealed within the finished condom body, resulting in a superior banded collagen condom according to the invention.

EXAMPLE 6

Comparative Tests

The strength of the integral elastic banding of the invention was compared with the prior art in a series of experiments.

A ¼ inch ring containing the rubber band was cut from 8 condoms of each type. The force required to break the collagen ring enclosing the rubber band was measured on an Instron testing machine. As shown in TABLE 1, the average breaking force for rings from condoms made on cone-shaped mandrels by folding the flap over the band was 6.24 kg. The average force required to break rings from condoms made on straight mandrels by dipping over the bands was 4.32 kg.

In operation, the banded condom according to the invention, comprising a solidified collagen gel and an integrated elastic band, provides superior strength, comfort, and reliability——all at relatively low cost.

The elastic bands are held more securely in condoms banded using the method of the invention. This is important because inadvertent separation of the band from the condom sheath can cause the condom to fail, and may result in an undesired pregnancy.

TABLE 1

| BREAKING FORCE (Kg) OF COLLAGEN RING ENCOMPASSING BAND | |
|---|---|
| THE INVENTION CONED MANDREL FLAP OVER BAND | THE PRIOR ART STRAIGHT MANDREL DIPPED OVER BAND |
| CONDOM 1 6.70 | 3.71 |
| CONDOM 2 5.52 | 4.25 |
| CONDOM 3 5.00 | 4.55 |
| CONDOM 4 7.18 | 4.31 |
| CONDOM 5 6.11 | 4.09 |
| CONDOM 6 5.29 | 5.23 |
| CONDOM 7 7.40 | 3.31 |
| CONDOM 8 6.75 | 5.07 |
| AVERAGE 6.24 Kg | 4.32 Kg |

It will be understood by skilled practitioners that the foregoing description and examples are illustrative, and do not serve to limit the scope of the invention or the appended claims.

We claim:

1. A method of banding collagen condoms comprising the steps of:

placing an elastic glue-free band in a first band position on a phallic mandrel having a head and a tail end, the first position being proximate to the tail end;

applying a coat of regenerated collagen gel over a body region of said mandrel extending from the head toward the tail end, the body region approaching, but not including, the first band position;

drying the coat to form a corresponding collagen film layer having a size and shape corresponding to the mandrel over the body region, said coat being open toward the tail end;

repeating said applying and drying steps a predetermined number of times to form a corresponding number of integrated inner collagen film layers extending over the body region, each of the layers having a homogeneous composition and a predetermined thickness, the layers together forming an inner sheath extending over the body region of the mandrel;

displacing the elastic band in the direction of the head of the mandrel to a final band position proximate to the open end and encircling the inner sheath;

moistening at least a portion of a tailward region of the inner sheath proximate to the elastic band in its final band position, the tailward region terminating at said open end;

applying a coat of the regenerated collagen gel to a headward region of the inner sheath proximate to the elastic band in its final band position;

folding at least a portion of the moistened tailward region over the elastic band in its final band position, the folded part forming at least one flap having an inner and an outer surface;

contacting at least part of the inner surface of the flap with the coated headward region, thereby enfolding the elastic band;

resuming and repeating said applying and drying steps a predetermined number of times to form a corresponding number of integrated outer collagen film layers extending over the body region and covering the final banding position, the outer layers forming an outer sheath, the elastic band being enveloped by the inner and outer sheaths, the sheaths together forming a condom body having the elastic band incorporated therein as an integral part thereof; and removing the condom body integral with the elastic band from the mandrel.

2. A method according to claim 1, wherein said flap is in the form of one unbroken circumferential cuff.

3. A method according to claim 2 wherein said cuff is in the shape of a section of a cone.

4. A method according to claim 3 wherein said mandrel is provided with a cone-shaped tailward extension, at least part of which is included within said body region.

5. A method according to claim 1 wherein said applying and drying steps provide that each said layer is of predetermined and uniform length and thickness.

6. A method according to claim 1, wherein said applying step comprises dipping said mandrel headfirst into a bath of said regenerated collagen gel.

7. A method according to claim 1 wherein said repeating and resuming steps are performed between one and two times, thereby providing an inner sheath having from two to three integral film layers, and an outer sheath having from one to two said film layers.

8. A method according to claim 1 wherein said drying step is performed in a drying tunnel.

9. A method according to claim 6 wherein said mandrel is plastic and wherein said mandrel is rotated during at least said dipping step.

10. A method according to claim 1 wherein said folding and contacting steps comprise blowing compressed air against said moistened tailward portion at a predetermined angle.

11. A method according to claim 2 wherein said folding and contacting steps comprise blowing compressed air against said moistened tailward portion at a predetermined angle.

12. A method according to claim 3 wherein said folding and contacting steps comprise blowing compressed air against said moistened tailward portion at a predetermined angle.

* * * * *